(12) United States Patent
Gysling

(10) Patent No.: US 7,363,800 B2
(45) Date of Patent: Apr. 29, 2008

(54) APPARATUS AND METHOD FOR MEASURING COMPOSITIONAL PARAMETERS OF A MIXTURE

(75) Inventor: Daniel L. Gysling, Glastonbury, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

(21) Appl. No.: 11/130,689

(22) Filed: May 17, 2005

(65) Prior Publication Data

US 2006/0037385 A1 Feb. 23, 2006

Related U.S. Application Data

(60) Provisional application No. 60/576,951, filed on Jun. 4, 2004, provisional application No. 60/571,904, filed on May 17, 2004.

(51) Int. Cl.
*G01N 9/24* (2006.01)
*G01N 9/32* (2006.01)
*G01N 29/14* (2006.01)
*G01N 29/22* (2006.01)

(52) U.S. Cl. .................. 73/19.01; 73/61.41; 73/61.43; 702/23; 702/25

(58) Field of Classification Search ............... 73/19.01, 73/32 R, 30.01–30.04, 31.05, 53.03, 53.04, 73/61.71, 61.75, 61.78, 61.79, 866.5; 702/23, 702/25, 137
See application file for complete search history.

(56) References Cited

U.S. PATENT DOCUMENTS

| | | | |
|---|---|---|---|
| 2,874,568 A | 2/1959 | Petermann | 73/861.02 |
| 4,004,461 A | 1/1977 | Lynworth | 73/861.27 |
| 4,048,853 A | 9/1977 | Smith et al. | 73/861.25 |
| 4,080,837 A | 3/1978 | Alexander et al. | 73/61.45 |
| 4,195,517 A | 4/1980 | Kalinoski et al. | 73/461.27 |
| 4,248,085 A | 2/1981 | Coulthard | 73/861.06 |
| 4,445,389 A | 5/1984 | Potzick et al. | 73/861.27 |
| 4,689,988 A | 9/1987 | Rydefalk et al. | |
| 4,896,540 A | 1/1990 | Shakkottai et al. | 73/861.02 |
| 5,040,415 A | 8/1991 | Barkhoudarian | 73/861.03 |
| 5,083,452 A | 1/1992 | Hope | 73/61 R |
| 5,224,372 A | 7/1993 | Kolpak et al. | |

(Continued)

FOREIGN PATENT DOCUMENTS

DE 203 05 448 U1 7/2003

(Continued)

OTHER PUBLICATIONS

"Clamp On, Sonar-Based Entrained Air Measurement for Pulp and Paper Applications", vol. 2, Jan. 27, 2004—pp. B-109-B-111, XP009056883—By: Daniel L. Gysling et al.

(Continued)

*Primary Examiner*—Daniel S. Larkin
*Assistant Examiner*—David A. Rogers
(74) *Attorney, Agent, or Firm*—Michael Grillo

(57) ABSTRACT

An apparatus for measuring compositional parameters of solid, liquid, and gas components of a mixture flowing in a pipe is presented. The apparatus combines three different compositional measurements (e.g., the speed of light (microwave), the speed of sound (sonar), and mass loading of vibrating tubes or absorption of radiation) simultaneously to provide a real time, multi parameter, compositional measurement of gas-entrained mixtures.

28 Claims, 5 Drawing Sheets

U.S. PATENT DOCUMENTS

| | | | |
|---|---|---|---|
| 5,250,807 A | 10/1993 | Sontvedt et al. | |
| 5,285,675 A | 2/1994 | Colgate et al. | 73/23.2 |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,535,632 A | 7/1996 | Kolpak et al. | |
| 5,591,922 A | 1/1997 | Segeral et al. | 73/861.04 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,856,622 A | 1/1999 | Yamamoto et al. | 73/861.28 |
| 5,948,959 A | 9/1999 | Peloquin | 73/1.83 |
| 6,151,958 A | 11/2000 | Letton et al. | 73/61.79 |
| 6,202,494 B1 | 3/2001 | Ricbel et al. | 73/861.29 |
| 6,354,147 B1 | 3/2002 | Gysling et al. | |
| 6,378,357 B1 | 4/2002 | Han et al. | 73/54.41 |
| 6,397,683 B1 | 6/2002 | Hagenmeyer et al. | 73/861.18 |
| 6,435,030 B1 | 8/2002 | Gysling et al. | |
| 6,450,037 B1 | 9/2002 | Davis et al. | |
| 6,463,813 B1 | 10/2002 | Gysling et al. | |
| 6,532,827 B1 | 3/2003 | Ohnishi | 73/861.27 |
| 6,536,291 B1 | 3/2003 | Gysling et al. | |
| 6,587,798 B2 | 7/2003 | Gysling et al. | |
| 6,601,458 B1 | 8/2003 | Gysling et al. | |
| 6,609,069 B2 | 8/2003 | Gysling | |
| 6,691,584 B2 | 2/2004 | Gysling et al. | |
| 6,698,297 B2 | 3/2004 | Gysling | |
| 6,732,575 B2 | 5/2004 | Gysling et al. | |
| 6,782,150 B2 | 8/2004 | Davis et al. | |
| 6,813,962 B2 | 11/2004 | Gysling et al. | |
| 6,837,098 B2 | 1/2005 | Gysling et al. | |
| 6,862,920 B2 | 3/2005 | Gysling et al. | |
| 6,889,562 B2 | 5/2005 | Gysling et al. | |
| 6,898,541 B2 | 5/2005 | Gysling et al. | |
| 6,945,095 B2 | 9/2005 | Johansen | 73/861.18 |
| 6,950,760 B2 | 9/2005 | Henry et al. | 702/45 |
| 6,959,604 B2 | 11/2005 | Davis et al. | |
| 6,971,259 B2 | 12/2005 | Gysling | |
| 6,988,411 B2 | 1/2006 | Gysling et al. | |
| 7,032,432 B2 | 4/2006 | Gysling et al. | |
| 2002/0014105 A1 | 2/2002 | Jakkula et al. | |
| 2002/0066304 A1* | 6/2002 | Jakkula et al. | 73/53.03 |
| 2003/0084707 A1* | 5/2003 | Gysling | 73/32 A |
| 2003/0089161 A1 | 5/2003 | Gysling | |
| 2003/0136186 A1 | 7/2003 | Gysling | |
| 2003/0154036 A1 | 8/2003 | Gysling et al. | |
| 2004/0069069 A1 | 4/2004 | Croteau | |
| 2004/0074312 A1 | 4/2004 | Gysling | |
| 2004/0144182 A1 | 7/2004 | Gysling et al. | |
| 2004/0168522 A1 | 9/2004 | Bailey et al. | |
| 2004/0168523 A1 | 9/2004 | Bailey et al. | |
| 2004/0194539 A1 | 10/2004 | Gysling | |
| 2004/0199340 A1 | 10/2004 | Gysling et al. | |
| 2004/0199341 A1 | 10/2004 | Gysling et al. | |
| 2004/0210404 A1 | 10/2004 | Gysling et al. | |
| 2004/0255695 A1 | 12/2004 | Gysling et al. | |
| 2005/0005711 A1 | 1/2005 | Curry et al. | |
| 2005/0005912 A1 | 1/2005 | Gysling et al. | |
| 2005/0011258 A1 | 1/2005 | Didden et al. | |
| 2005/0011283 A1 | 1/2005 | Gysling et al. | |
| 2005/0011284 A1 | 1/2005 | Davis et al. | |
| 2005/0033545 A1 | 2/2005 | Gysling | |
| 2005/0039520 A1 | 2/2005 | Bailey et al. | |
| 2005/0044929 A1 | 3/2005 | Banach et al. | |
| 2005/0050956 A1 | 3/2005 | Croteau et al. | |
| 2005/0061060 A1 | 3/2005 | Banach et al. | |
| 2005/0125166 A1 | 6/2005 | Davis et al. | |
| 2005/0125169 A1 | 6/2005 | Loose | |
| 2005/0125170 A1 | 6/2005 | Gysling | |
| 2005/0171710 A1 | 8/2005 | Gysling et al. | |
| 2005/0227538 A1 | 10/2005 | Engel | |
| 2005/0246111 A1 | 11/2005 | Gysling et al. | |
| 2006/0048583 A1 | 3/2006 | Gysling | |
| 2006/0053809 A1 | 3/2006 | Gysling et al. | |

FOREIGN PATENT DOCUMENTS

| | | |
|---|---|---|
| WO | WO 93/14382 | 7/1993 |
| WO | WO 99/67629 | 12/1999 |
| WO | WO 00/60317 | 10/2000 |
| WO | WO 01/02810 | 1/2001 |
| WO | WO 2004/065913 | 8/2004 |
| WO | WO 04065912 | 8/2004 |
| WO | WO 05010470 | 2/2005 |

OTHER PUBLICATIONS

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attentuation of Acoustic Waves in Suspensions" by R.L. Gibson, Jr. and M.N. Toksoz.

Sonar-Based Volumetric Flow Meter for Pulp and Paper Applications—By: Daniel L. Gysling & Douglas H. Loose—Dec. 3, 2002.

Sonar Based Volumetric Flow Meter for Chemical and Petrochemical Applications—By: Daniel L. Gysling & Douglas H. Loose—Feb. 14, 2003.

Sonar Based Volumetric Flow and Entrained Air Measurement for Pulp and Paper Applications—By: Daniel L. Gysling & Douglas H. Loose—Jan. 24, 2003.

"New Flowmeter Principle"—By: Walt Boyes—Published in Flow Control Magazine—Oct. 2003 Issue.

"Piezoelectric Polymers"—By: J.S. Harrison and Z. Ounaies—ICASE Report.

* cited by examiner

APPARATUS AND METHOD FOR MEASURING COMPOSITIONAL PARAMETERS OF A MIXTURE

CROSS-REFERENCE TO RELATED PATENT APPLICATIONS

The present invention claims the benefit of U.S. Provisional Patent Application No. 60/571,904 filed May 17, 2004, and U.S. Provisional Patent Application No. 60/576,951 filed Jun. 4, 2004, which are all incorporated herein by reference.

BACKGROUND

The present disclosure relates to an apparatus and method for measuring compositional parameters of a mixture flowing in a pipe. More particularly the present disclosure relates to an apparatus and method for measuring compositional parameters such as volume fraction, volumetric flow rate, and the like of solid, liquid, and gas components of a mixture flowing in a pipe.

Fluid processes are found in many different industries such as, for example: oil and gas, refining, food and beverage, chemical and petrochemical, pulp and paper, power generation, pharmaceutical, manufacturing, water and wastewater, among others. Such processes typically include process monitoring equipment, which determine parameters of the fluid such as flow rate, density, composition, and the like. For example, in the pulp and paper industry, process monitoring equipment is used to precisely monitor the content of paper and pulp slurries, white water, and other mixtures. In another example, process monitoring equipment is used in the oil and gas industry to determine the level of solids production while testing the flow rates of fluids produced from an oil and gas well.

Problematically, entrained gas in the process flow results in measurement errors in the process monitoring equipment. For example, since most flow meters are unable to distinguish between air and liquid, interpreting their output as liquid flow rates would result in a overestimate of the liquid by the volumetric flow rate of the air present at the measurement location. Similarly, the void fraction of the air within the pipe can cause errors in consistency measurements. Indeed, microwave consistency meters, nuclear based density meters, Coriolis (vibrating tube) density meters, and other meters for the real-time monitoring of compositional parameters are all confounded by an unknown amount of aeration. While these meters still report a measurement for the aerated fluid, its interpretation in terms of the composition of liquid (with or without solids) is significantly impaired.

Because of these measurement errors, determining the compositional parameters of aerated fluids remains a challenge, and most compositional analysis is done using the time-consuming process of extracting samples of the mixture from the process on a periodic basis and testing the samples in a lab.

Methods have been devised to correct various meters for entrained gas. For example, U.S. Patent Application Publication No. 2004/0255695 published Dec. 23, 2004 and entitled "Apparatus and Method for Providing a Flow Measurement Compensated for Entrained Gas," which is incorporated by reference herein in its entirety, describes an apparatus that measures the speed of sound and/or vortical disturbances propagating in a fluid or mixture having entrained gas/air to determine the gas volume fraction (GVF) of the flow propagating through a pipe and compensating or correcting the volumetric flow measurement for entrained air. The GVF meter includes an array of sensors disposed axially along the length of the pipe. The GVF meter measures the speed of sound propagating through the pipe and fluid to determine the gas volume fraction of the mixture using array processing. The GVF meter can be used with an electromagnetic meter and a consistency meter to compensate for volumetric flow rate and consistency measurements respectively, to correct for errors due to entrained gas.

In another example, U.S. Patent Application Publication No. 2005/0044929 published Mar. 3, 2005 and entitled "Apparatus and Method for Compensating a Coriolis Meter," which is incorporated by reference herein in its entirety, describes a flow measuring system that provides at least one of a compensated mass flow rate measurement and a compensated density measurement. The flow measuring system includes a gas volume fraction meter in combination with a Coriolis meter. The GVF meter measures acoustic pressures propagating through the fluids to measure the speed of sound propagating through the fluid to calculate at least gas volume fraction of the fluid and/or the reduced natural frequency. For determining an improved density for the Coriolis meter, the calculated gas volume fraction and/or reduced frequency is provided to a processing unit. The improved density is determined using analytically derived or empirically derived density calibration models (or formulas derived therefore), which is a function of the measured natural frequency and at least one of the determined GVF, reduced frequency and speed of sound, or any combination thereof. The gas volume fraction (GVF) meter may include a sensing device having a plurality of strain-based or pressure sensors spaced axially along the pipe for measuring the acoustic pressures propagating through the flow.

In another example, U.S. Patent Application Publication No. 2005/0061060 published Mar. 24, 2005 and entitled "Apparatus and Method for Providing a Density Measurement Augmented for Entrained Gas," which is incorporated by reference herein in its entirety, describes a flow measuring system that combines a density measuring device and a device for measuring the speed of sound (SOS) propagating through the fluid flow and/or for determining the gas volume fraction (GVF) of the flow. The GVF meter measures acoustic pressures propagating through the fluids to measure the speed of sound propagating through the fluid to calculate at least gas volume fraction of the fluid and/or SOS. In response to the measured density and gas volume fraction, a processing unit determines the density of non-gaseous component of an aerated fluid flow. For three phase fluid flows, the processing unit can determine the phase fraction of the non-gaseous components of the fluid flow. The gas volume fraction (GVF) meter may include a sensing device having a plurality of strain-based or pressure sensors spaced axially along the pipe for measuring the acoustic pressures propagating through the flow.

There remains, however, a need for an apparatus and method for measuring compositional parameters such as volume fraction, volumetric flow rate, and the like of solid, liquid, and gas components of a mixture flowing in a pipe, particularly where it is desired to determine a concentration of each of two or more solids or each of two or more liquids in a multi-phase mixture including entrained gas.

SUMMARY

In one aspect, there is provided a method and apparatus for measuring parameters of a mixture flowing in a pipe, where the mixture includes at least two solids, a liquid, and a gas. The apparatus comprises a first device that senses at least one parameter of the mixture indicative of a density of the mixture and provides a first signal indicative of the density. A second device senses at least one parameter of the mixture indicative of a combined concentration of the at least two solids in the mixture and provides a second output signal indicative of the combined concentration of the solids. A third device senses at least one parameter of the mixture indicative of a concentration of the gas in the mixture and provides a third signal indicative of the concentration of the gas. A signal processor receives the first, second, and third signals and determines a concentration of each of the at least two solids and a concentration of the liquid using the density of the mixture, the combined concentration of the at least two solids, and the concentration of the gas.

The first device may include at least one of a Coriolis meter and a gamma densitometer. The second device may include a consistency meter, and the third device may include a spatial array of at least two pressure sensors disposed at different axial locations along the pipe. Each of the at least two pressure sensors provide a pressure signal indicative of unsteady pressure within the pipe at a corresponding axial location, where the unsteady pressure is caused at least in part by acoustic pressure disturbances in the mixture.

In another aspect, there is provided a method and apparatus for measuring parameters of a mixture flowing in a pipe, where the mixture includes at least two liquids, a solid, and a gas. The apparatus comprises a first device that senses at least one parameter of the mixture indicative of a density of the mixture and provides a first signal indicative of the density. A second device senses at least one parameter of the mixture indicative of a concentration of a liquid in the at least two liquids and provides a second output signal indicative of the concentration of the liquid. A third device senses at least one parameter of the mixture indicative of a concentration of the gas in the mixture and provides a third signal indicative of the concentration of the gas. A signal processor receives the first, second, and third signals and determines a concentration of each of the at least two liquids and a concentration of the solid using the density of the mixture, the concentration of the liquid, and the concentration of the gas. The signal processor may be further configured to determine a volumetric flow rate of each of the at least two liquids using the concentration of each of the at least two liquids.

The first device may include at least one of a Coriolis meter and a gamma densitometer. The second device may include a water cut meter, and the third device may include a spatial array of at least two pressure sensors disposed at different axial locations along the pipe. Each of the at least two pressure sensors provides a pressure signal indicative of unsteady pressure within the pipe at a corresponding axial location, with the unsteady pressure being caused at least in part by acoustic pressure disturbances in the mixture.

BRIEF DESCRIPTION OF THE DRAWINGS

Referring now to the Drawing wherein like items are numbered alike in the various Figures.

DETAILED DESCRIPTION

Figure 1:
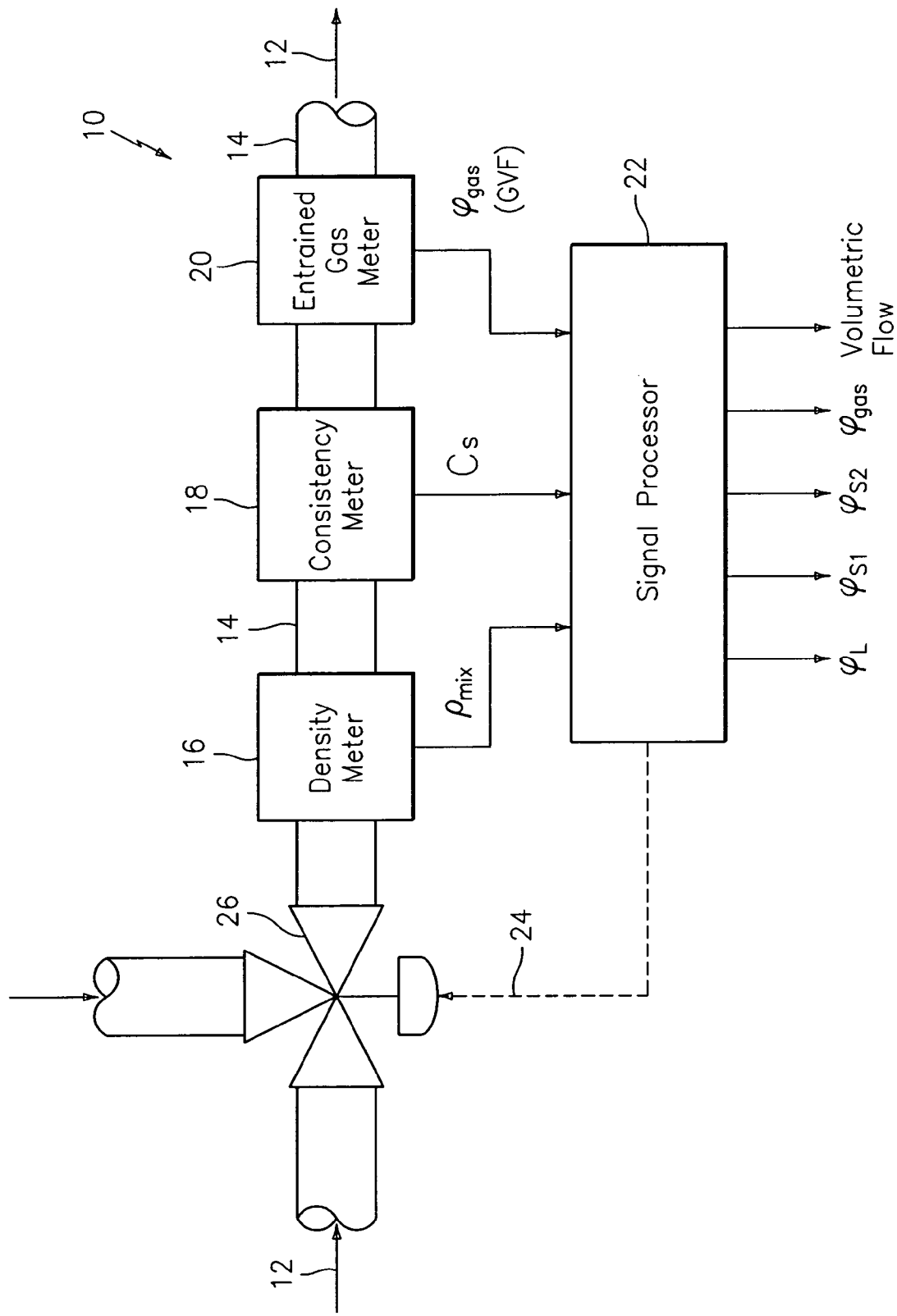
FIG. 1 is a schematic illustration of an apparatus for measuring compositional parameters of the solid, liquid, and gas components of a mixture flowing in a pipe.

FIG. 1 depicts a first embodiment of an apparatus 10 for measuring compositional parameters of the solid, liquid, and gas components of a mixture 12 flowing in a pipe, duct, channel, conduit, or the like (hereinafter "pipe") 14. As described in further detail hereinafter, the apparatus 10 combines three separate, compositional measurements of the mixture 12 to provide a real time, multi parameter, compositional measurement of the mixture 12. The apparatus 10 includes: a first device 16 that senses at least one parameter of the mixture 12 indicative of a density of the mixture 12 and provides a signal indicative of the density ($\rho_{mix}$); a second device 18 that senses at least one parameter of the mixture 12 indicative of a concentration (e.g., a mass or volume fraction) of a component of the mixture and provides a signal indicative of the concentration (Cs); and a third device 20 that senses at least one parameter of the mixture 12 indicative of a concentration of gas in the mixture and provides a signal indicative of the concentration (gas volume fraction (GVF)). The apparatus 10 further includes a signal processor 22 that receives signals from each of the devices 16, 18, and 20 and, using the input from these apparatuses, determines a concentration of the liquids and solids in the mixture ($\varnothing_L$, $\varnothing_{S1}$, $\varnothing_{S2}$, $\varnothing_{gas}$). As used herein, the term "concentration" includes mass fraction or ratio, volume fraction or ratio, and the like.

Once the concentration of the components ($\varnothing_L$, $\varnothing_{S1}$, $\varnothing_{S2}$, $\varnothing_{gas}$) are determined, the signal processor 22 may use these values to calculate other compositional parameters such as, for example, volumetric flow rate of one or more of the components. The compositional parameters from the signal processor 22 may be provided as feedback in a control loop 24 for the associated process. For example, the process may adjust a mixing valve 26 to change the amount of one or more components of the mixture 12 in response to the feedback from the apparatus 10.

Each of the three devices 16, 18, and 20 senses a different parameter of the mixture 12. The first device 16 senses any parameter of the mixture 12 that indicates density of the mixture. For example, the first device 16 may include a Coriolis meter, which senses mass loading of vibrating tubes through which the mixture flows, and characterizes the aeroelastic response of the fluid-filled, vibrating tubes to determine the density of the mixture 12 flowing through the tubes. The Coriolis meter may be any known Coriolis meter, such as two inch bent tube Coriolis meter manufactured my MicroMotion Inc. and a two in straight tube Coriolis meter manufactured by Endress & Hauser Inc.

Alternatively, devices other than a Coriolis meter may be used to determine density of the mixture 12. For example, a gamma (radiation) densitometer, which senses the absorption of radiation by the mixture, may be used as the first device 16.

In the embodiment of FIG. 1, the second device 18 senses any parameter of the mixture 12 that indicates a combined concentration of the solid components of the mixture 12. For example, the second device 18 may be a consistency meter that determines a mass or volume fraction of the solids in the mixture 12.

The parameter sensed by the second device 18 to determine the consistency of the mixture may include one or more of: absorption, attenuation, time delay, and phase delay of energy applied to the mixture 12. For example, microwave consistency meters apply energy to the mixture 12 in the form of microwaves. One type of microwave consistency meter measures speed or velocity at which the microwave signal propagates through the mixture 12. The velocity of the microwave signal propagating through the mixture 12 is measured by the conductive effects of the mixture, in accordance with the following equation:

$$V = c * \text{sqrt}(E)$$

where V is the velocity of the microwave signal propagating through the mixture 12, c is the speed of light in a vacuum, and E is the relative conductivity of the material. Typical values of relative conductivity for material comprising a paper/pulp slurry, for example, are:
Water relative conductivity=80;
Air relative conductivity=1; and
Fiber relative conductivity=3.

One such microwave-based consistency meter is manufactured by Toshiba International Corporation of Japan.

Another type of microwave consistency meter uses a measurement principle based on the correlation between consistency and microwave time of flight. An example of this type of microwave consistency meter is manufactured by Metso Automation of Finland and sold under the trade name kajaaniMCA™. These "time of flight" microwave consistency meters operate on the principle that solids, such as fibers and fillers, conduct the microwaves faster than water so that shorter transit times are seen with higher consistencies.

Another type of consistency meter employs a small gamma source, which is attenuated as it passes through the pulp stock. The attenuation, which is detected by a scintillation detector, is proportional to the changes in consistency. This type of consistency meter is commercially available from Berthold Industrial Systems of Australia. Other parameters that may be sensed by the second device 18 to determine the consistency of the mixture include capacitance and conductance of the mixture.

The third device 20 senses any parameter of the mixture 12 that indicates a concentration of gas in the mixture 12. For example, the third device 20 may include a GVF meter that employs a sensing device having a plurality of strain-based or pressure sensors spaced axially along the pipe 14 for measuring the acoustic pressures propagating through the mixture 12. The GVF meter measures acoustic pressures propagating through the mixture 12 to measure the speed of sound $\alpha_{mix}$. The GVF meter calculates at least gas volume fraction of the mixture 12 using the measured speed of sound, as is described in further detail hereinafter. The GVF meter may also use the pressure of the process flow to determine the gas volume fraction. The pressure may be measured or estimated. The GVF meter is similar to that described in U.S. patent application Ser. No. 10/762,410 filed Jan. 21, 2004, which is incorporated herein by reference.

Figure 2:
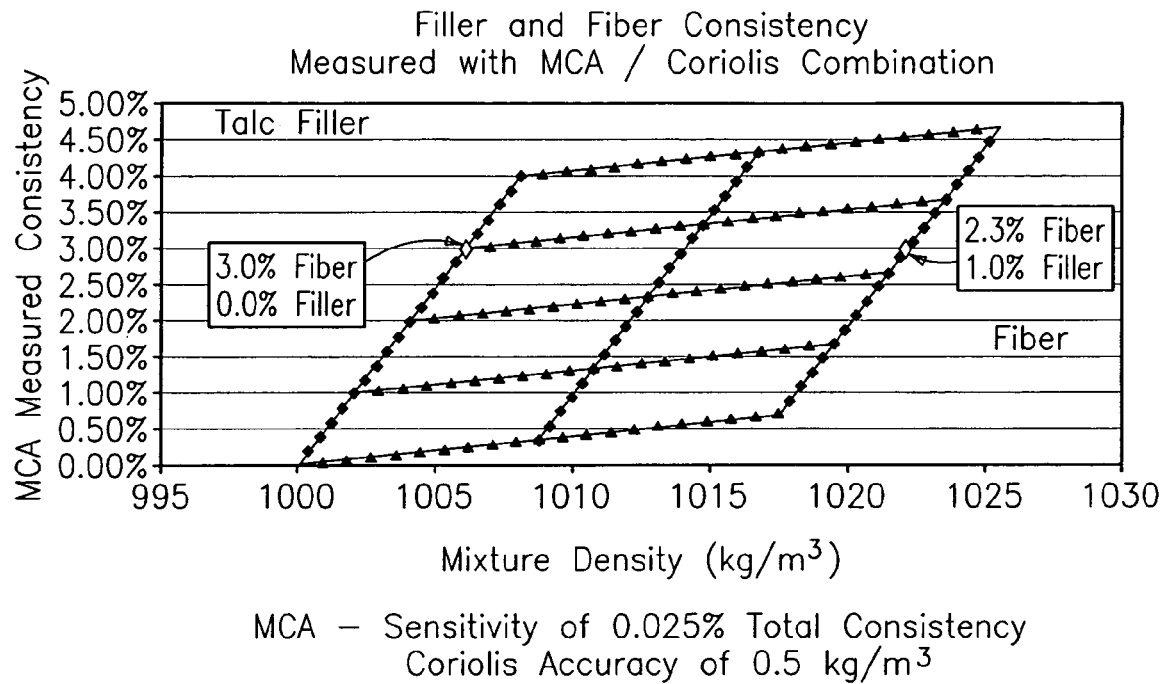
FIG. 2 is a plot depicting a relationship between measured consistency, as measured with a time-of-flight type microwave consistency meter, and mixture density, as measured with a Coriolis meter, for a range of wood fiber (0-4%) and calcium carbonate filler (0-1%) consistencies in a non-aerated suspension.

FIG. 2 depicts a relationship between measured consistency, as measured with a time-of-flight type microwave consistency meter, and mixture density, as measured with a Coriolis meter, for a range of wood fiber (0-4%) and talc filler (0-1%) consistencies in a non-aerated suspension. As shown, each combination of filler and fiber consistencies occupies a unique point in the plot. The plot also illustrates the inability of either the density or consistency measurement alone to provide a unique measurement of fiber and/or filler consistency. For example, a mixture with 3% fiber and 0% filler has the same consistency measurement as a mixture of 2.3% fiber and 1% filler. Although these two mixtures have the same consistency measurement, they have appreciably different mixture densities, 1005 kg/m^3 and 1022 kg/m^3, respectively. Thus, for non-aerated mixtures, both consistency and mixture density measurements are needed to determine a unique measurement of fiber and/or filler consistency.

Problematically, the inclusion of entrained air or other gasses into the mixture results in measurement errors in the consistency and density measurements. For example, the void fraction of the air within the pipe can cause errors in consistency measurements. For Coriolis meters, some of the fundamental assumptions regarding the interaction of the fluid and the structure can deteriorate under different operating conditions. Specifically, aerated fluids in oscillating tubes behave differently from single phase fluids, which results in measurement error. The uncertainty resulting from such measurement errors prevents the consistency and mixture density measurements from being relied upon to determine a unique measurement of fiber and/or filler consistency when entrained gas is present in the mixture. As a solution to this, the microprocessor of FIG. 1 combines three different compositional measurements (e.g., the speed of light (microwave), the speed of sound (sonar), and mass loading of vibrating tubes or absorption of radiation) simultaneously to provide a real time, multi parameter, compositional measurement of aerated mixtures.

Referring again to FIG. 1, in operation, the signal processor 22 receives a signal indicating the density of the mixture 12 ($\rho_{mix}$) from the first device 16, a signal from the second device 18 indicating the concentration (e.g., mass or volume fraction) of the solids in the mixture 12 (Cs) (e.g., the consistency of the mixture 12), and a signal indicating the volume fraction of the gas (GVF) from the third device 20. Using this data along with predetermined values for densities ($\rho_L$, $\rho_{S1}$, $\rho_{S2}$, $\rho_{gas}$) and measurement-specific sensitivity parameters ($\alpha_L$, $\alpha_{S1}$, $\alpha_{S2}$, $\alpha_{gas}$) of the liquid (L), first solid (S1), second solid (S2), and gas (gas) components, respectively, the signal processor 22 solves the following set of four coupled, linear equations for the concentration of the components ($\phi_L$, $\phi_{S1}$, $\phi_{S2}$, $\phi_{gas}$) of the mixture 12:

$$\begin{bmatrix} \rho_L & \rho_{S1} & \rho_{S2} & \rho_{gas} \\ \alpha_L \frac{\rho_L}{\rho_{mix}} & \alpha_{S1} \frac{\rho_{S1}}{\rho_{mix}} & \alpha_{S2} \frac{\rho_{S2}}{\rho_{mix}} & \alpha_{gas} \frac{\rho_{gas}}{\rho_{mix}} \\ 0 & 0 & 0 & 1 \\ 1 & 1 & 1 & 1 \end{bmatrix} \begin{Bmatrix} \phi_L \\ \phi_{S1} \\ \phi_{S2} \\ \phi_{gas} \end{Bmatrix} = \begin{Bmatrix} \rho_{mix} \\ Cs \\ GVF \\ 1 \end{Bmatrix} \quad (1)$$

In the set of coupled equations (1), the concentration of the components ($\emptyset_L$, $\emptyset_{S1}$, $\emptyset_{S2}$, $\emptyset_{gas}$) is a volume fraction of the mixture 12. It will be appreciated, however, that the equations (1) may be modified to provide a mass fraction of the mixture 12.

For example, where the mixture 12 is white water from a paper machine, the liquid component (L) is primarily water, the first solid (S1) is wood fiber, the second solid (S2) is a filler, and the gas is primarily air. White water is the primarily liquid mixture that drains off of paper sheet during a paper manufacturing process. It has a significant amount of chemical additives, is aerated, and contains some fiber. Precise monitoring the content of the white water allows the a high degree of optimization in the paper making process.

In this example, the densities ($\rho_L$, $\rho_{S1}$, $\rho_{S2}$, $\rho_{gas}$) of the components of the mixture 12 are known, or at least can be estimated. Table 1 provides approximate densities of wood fiber, common fillers, and air. The filler density can be estimated from the known constituents of the filler, for example, 20% talc and 80% clay.

TABLE 1

Approximate values for Microwave Sensitivity and Density of Fiber, common fillers, and air.

| Material | Microwave Sensitivity | Density (kg/m^3) |
| --- | --- | --- |
| Wood Fiber | 1 | 1200 |
| Talc | 0.70 | 2750 |
| Clay | 0.62 | 1800 |
| Calcium Carbonate | 0.47 | 2700 |
| Titianium Dioxide (TiO2) | 0.1 | 4260 |
| Air (at STP) | 1.4 | 1.2 |

Table 1 also provides approximate sensitivity parameters, shown as microwave sensitivity, of wood fiber, common fillers, and air. The sensitivity parameters of the components ($\alpha_L$, $\alpha_{S1}$, $\alpha_{S2}$, $\alpha_{gas}$) quantify the effect of the component on the output of the consistency meter, and are associated with the type of consistency meter used. The values of Table 1 quantify the effect of the listed component materials on the output of a time-of-flight microwave consistency meter. For example, 1 part talc appears as a 0.70% change in total consistency as reported by the microwave consistency meter; and 1 part air results in a 1.4% change (increase) in the reported total consistency.

In the set of four coupled, linear equations (1) above, density variations are accounted for in the standard mixing rule for mixture density, a volume fraction weighted summation of densities to determine mixture density:

$$\rho_{mix} = \phi_L \rho_L + \phi_{S1} \rho_{S1} + \phi_{S2} \rho_{S2} + \phi_{gas} \rho_{gas} \quad (2)$$

In the case where the density of the mixture ($\rho_{mix}$) is measured using a Coriolis meter, it is contemplated that the density $\rho_{mix}$ may be corrected for entrained air using a method described in U.S. Patent Application Publication No. 2005/0044929 published Mar. 3, 2005 and entitled "Apparatus and Method for Compensating a Coriolis Meter," which is incorporated by reference herein in its entirety. Where GVF is determined using a sonar-based meter, as described herein, the GVF value is insensitive to filler and fiber consistency variations.

By solving the set of four coupled, linear equations (1), the signal processor 22 determines the volume fraction of the liquid (L), gas, and solid (S1 and S2) components ($\emptyset_L$, $\emptyset_{S1}$, $\emptyset_{S2}$, $\emptyset_{gas}$) of the mixture 12. The volume fraction of one or more of the components may be output by the signal processor 22. It is also contemplated that the volume fraction of one or more of the components may be used to determine other useful compositional information. For example, assuming a well-mixed flow, the signal processor 22 may calculate the volumetric flow rate of any of the components using the volume fraction of the component and the flow rate of the mixture 12. In another example, the signal processor 22 can convert the volume fraction of the solid components S1 and/or S2 to a mass fraction to determine the consistency of either solid S1 or S2 (e.g., the filler or the fiber). Such compositional information is useful, for example, in applications where it is necessary to accurately determine the amount of filler and fiber in the aerated liquid mixture 12. The apparatus 10 can provide any of these measurements simultaneously, in real-time.

Figure 3:
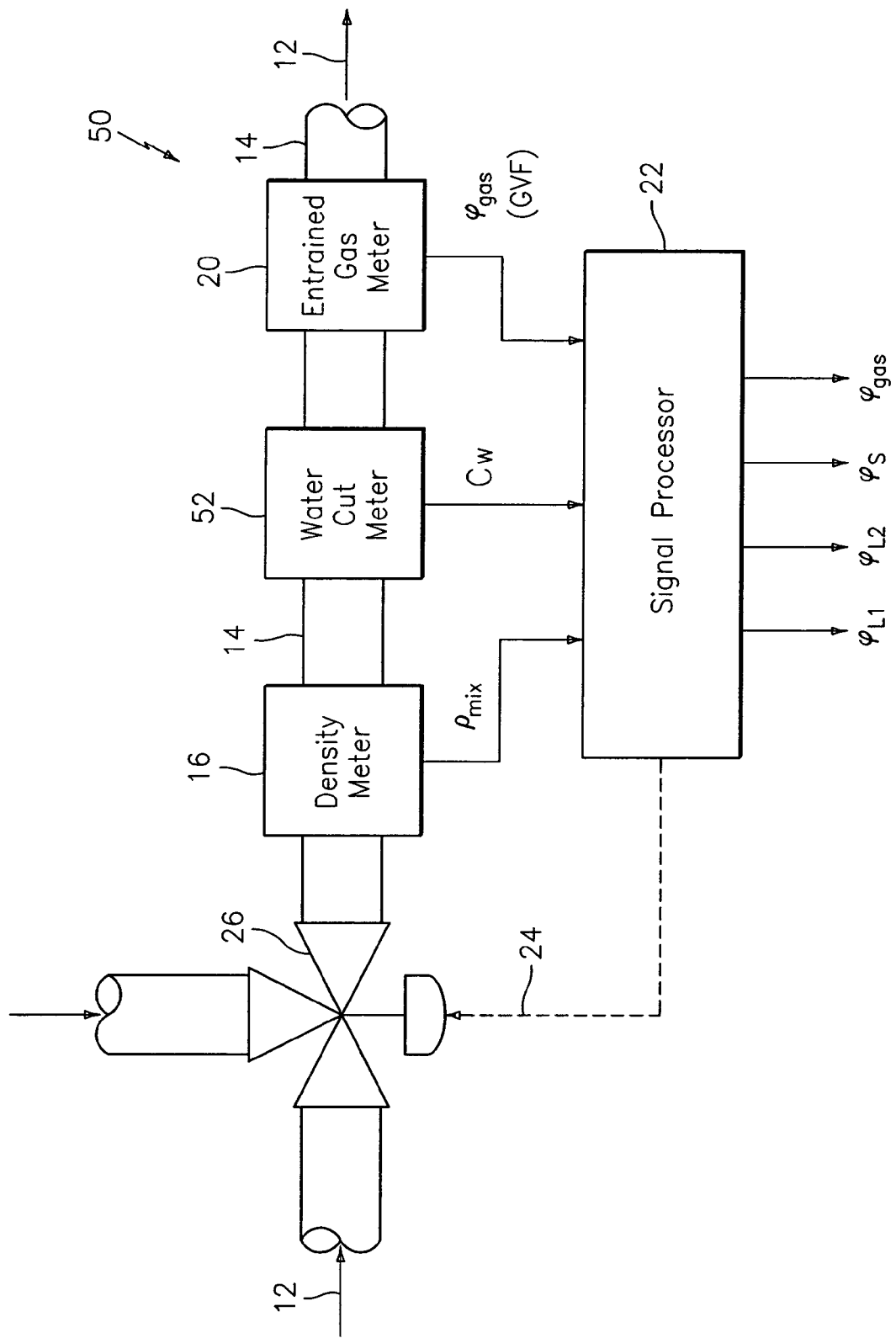
FIG. 3 is a schematic illustration of an alternative embodiment of an apparatus for measuring compositional parameters of the solid, liquid, and gas components of a mixture flowing in a pipe.

FIG. 3 depicts an embodiment of an apparatus 50 that may be used to determine a concentration of each of two liquids (L1) and (L2), a solid (S), and a gas component of the mixture 12. The apparatus 50 can provide a real-time measurement of the overall flow rate of the mixture 12 as well as the flow rates of the four components.

The embodiment depicted in FIG. 3 may be useful, for example, in the oil and gas industry where it is necessary to determine the amount of oil, water, and solids in the oil/water/gas/solids mixture. Typically, an oil and gas well produces variable amounts of oil, water, and gas. Most well testing uses some form of separation prior to measurement. Often, this separation is in the form of a gas/liquid separation, in which most of the gas is separated from the liquid. The result is two streams, one mostly gas, one mostly liquid. The liquid stream will consist mostly of oil and water, as well as a small amount of gas and a relatively large amount of produced solids. The apparatus 50 of FIG. 3 allows for the precise monitoring the content of this liquid stream.

The apparatus 50 of FIG. 3 is substantially similar to the apparatus 10 described above with reference to FIG. 1 and FIG. 2, except that, in the apparatus 50 of FIG. 3, a second device 52 senses a concentration of one of the liquid components of the mixture 12 and provides a signal indicative of this concentration (Cw) to the signal processor 22. Where the mixture 12 includes oil and water, the second device 52 may be, for example, a water-cut meter. One example of a water-cut meter is commercially available from Agar Corporation of Houston, Tex. This meter utilizes a microwave transmitter and two receivers to measure the bulk electrical properties of the liquids. The difference in dielectric properties of the two liquids is analyzed and translated into volumetric concentrations of the oil and water components of the mixture. The ratio of water volume to total mixture volume is known as "water cut".

In operation, the signal processor 22 receives a signal indicating the density of the mixture 12 ($\rho_{mix}$) from the first device 16, a signal indicating the concentration of the mixture 12 (Cw) (e.g., the water cut of the mixture) from the second device 52, and a signal indicating the volume fraction of the gas (GVF) from the third device 20. Using this data along with predetermined values for densities ($\rho_L$, $\rho_{S1}$, $\rho_{S2}$, $\rho_{gas}$) and measurement-specific sensitivity parameters ($\alpha_{L1}$, $\alpha_{L2}$, $\alpha_S$, $\alpha_{gas}$) of the first liquid (L1), second liquid (L2), solid (S), and gas (gas) components, respectively, the signal processor 22 solves the following set of four coupled, linear equations for the concentration of the components ($\emptyset_{L1}$, $\emptyset_{L2}$, $\emptyset_S$, $\emptyset_{gas}$) of the mixture 12:

$$\begin{bmatrix} \rho_{L1} & \rho_{L2} & \rho_S & \rho_{gas} \\ \alpha_{L1} & \alpha_{L2} & \alpha_S & \alpha_{gas} \\ 0 & 0 & 0 & 1 \\ 1 & 1 & 1 & 1 \end{bmatrix} \begin{Bmatrix} \phi_{L1} \\ \phi_{L2} \\ \phi_S \\ \phi_{gas} \end{Bmatrix} = \begin{Bmatrix} \rho_{mix} \\ C_{S_{MCA}} \\ EA_{SONAR} \\ 1 \end{Bmatrix} \quad (3)$$

In the set of coupled equations (3), the concentration of the components ($\phi_L$, $\phi_{S1}$, $\phi_{S2}$, $\phi_{gas}$) is a volume fraction of the mixture 12. It will be appreciated, however, that the equations (3) may be modified to provide a mass fraction of the mixture 12.

For example, where the mixture 12 includes oil, water, gas, and solids, as may be produced from an oil and gas well, the first liquid component (L1) is oil, the second liquid component (L2) is water, and the gas (gas) and solids (S) components are those gasses and solids typically associated with oil and gas well production. The densities ($\rho_{L1}$, $\rho_{L2}$, $\rho_S$, $\rho_{gas}$) of these components of the mixture are known, or at least can be estimated.

The measurement-specific sensitivity parameters of the components ($\alpha_{L1}$, $\alpha_{L2}$, $\alpha_S$, $\alpha_{gas}$) quantify the effect of the component on the output of the second device 52, and are associated with the type of meter used. Typically, a water cut meter will output only a volume or mass fraction of water in the mixture. Accordingly, where the second device is a water cut meter and L2 is the water component, $\alpha_{L2}$ will be the only non-zero sensitivity parameter in equation (3).

In the set of four coupled, linear equations (3) above, density variations are accounted for in the standard mixing rule for mixture density, a volume fraction weighted summation of densities to determine mixture density:

$$\rho_{mix} = \phi_{L1}\rho_{L1} + \phi_{L2}\rho_{L2} + \phi_S \rho_S + \phi_{gas}\rho_{gas} \quad (4)$$

In the case where the density of the mixture ($\rho_{mix}$) is measured using a Coriolis meter, the density $\rho_{mix}$ may be corrected for entrained air using a method described in U.S. Patent Application Publication No. 2005/0044929 published Mar. 3, 2005 and entitled "Apparatus and Method for Compensating a Coriolis Meter," which is incorporated by reference herein in its entirety. Where GVF is determined using a sonar-based meter, as described herein, the GVF value is insensitive to filler and fiber consistency variations.

By solving the set of four coupled, linear equations (3), the signal processor 22 determines the volume fraction of the solid (S), gas, and liquid (L1 and L2) components ($\phi_{L1}$, $\phi_{L2}$, $\phi_S$, $\phi_{gas}$) of the mixture 12. The volume fraction of one or more of the components may be output by the signal processor 22. It is also contemplated that the volume fraction of one or more of the components may be used to determine other useful compositional information. For example, assuming a well-mixed flow, the signal processor 22 may calculate a volumetric flow rate of any of the components using the volume fraction of the component and the flow rate of the mixture. The apparatus 50 can provide any of these measurements simultaneously, in real-time.

Figure 4:
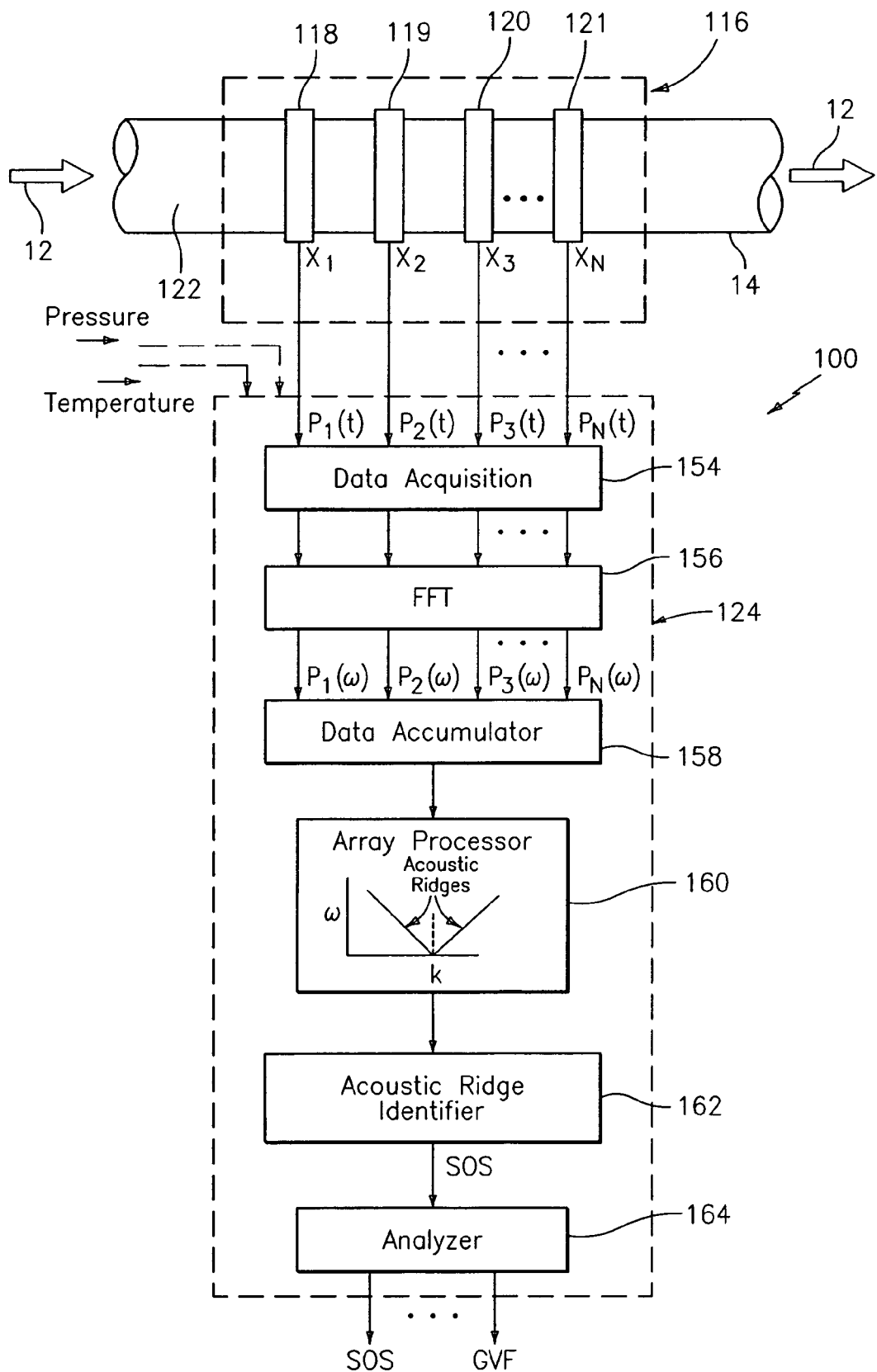
FIG. 4 is a schematic block diagram of a gas volume fraction meter that may be employed in the various embodiments of FIGS. 1-5.

FIG. 4 illustrates a gas volume fraction (GVF) meter, as may be used as the first device 16 of FIG. 1 and FIG. 3. The GVF meter includes a sensing device 116 disposed on the pipe 14 and a processing unit 124 operably coupled to the sensing device. The sensing device 116 comprises an array of at least two pressure sensors 118,119, located at at least two locations $x_1$ $x_2$ axially along the pipe 14 for sensing respective stochastic signals propagating between the sensors 118,119 within the pipe at their respective locations.

Each sensor 118,119 provides a signal indicating an unsteady pressure at the location of the sensor, at each instant in a series of sampling instants.

The sensor array may include more than two pressure sensors as depicted by pressure sensor 120,121 at locations $x_3, x_N$, respectively. The array of sensors of the sensing device 116 may include any number of pressure sensors 118-121 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the mixture. Therefore, the number of sensors used is dependent at least on the degree of accuracy desired and the desire update rate of the output parameter provided by the apparatus 100.

The pressure sensors 118-121 may be clamped onto or generally removably mounted to the pipe by any releasable fastener, such as bolts, screws and clamps. Alternatively, the sensors may be permanently attached to, ported in or integral (e.g., embedded) with the pipe 14.

The apparatus may include one or more acoustic sources 127 to enable the measurement of the speed of sound propagating through the mixture for instances of acoustically quiet flow. The acoustic source may be a device the taps or vibrates on the wall of the pipe, for example. The acoustic sources may be disposed at the input end of output end of the array of sensors 118-121, or at both ends as shown. One should appreciate that in most instances the acoustics sources are not necessary and the apparatus passively detects the acoustic ridge provided in the flow 12, as will be described in greater detail hereinafter. The passive noise includes noise generated by pumps, valves, motors, and the turbulent mixture itself.

The pressure generated by the acoustic pressure disturbances is measured through the pressure sensors 118-121, which provide analog pressure time-varying signals $P_1(t)$, $P_2(t), P_3(t), P_N(t)$ to the signal processing unit 124. The processing unit 124 processes the pressure signals to first provide output signals 151,155 indicative of the speed of sound propagating through the flow 12, and subsequently, provide a GVF measurement in response to pressure disturbances generated by acoustic waves propagating through the flow 12.

More specifically, the processing unit 124 receives the pressure signals from the array of sensors 118-121. A data acquisition unit 154 digitizes pressure signals $P_1(t)$-$P_N(t)$ associated with the acoustic waves 14 propagating through the pipe 114. An FFT logic 156 calculates the Fourier transform of the digitized time-based input signals $P_1(t)$-$P_N(t)$ and provide complex frequency domain (or frequency based) signals $P_1(\omega), P_2(\omega), P_3(\omega), P_N(\omega)$ indicative of the frequency content of the input signals.

A data accumulator 158 accumulates the additional signals $P_1(t)$-$P_N(t)$ from the sensors, and provides the data accumulated over a sampling interval to an array processor 160, which performs a spatial-temporal (two-dimensional) transform of the sensor data, from the xt domain to the k-$\omega$ domain, and then calculates the power in the k-$\omega$ plane, as represented by a k-$\omega$ plot, similar to that provided by the convective array processor 146.

To calculate the power in the k-$\omega$ plane, as represented by a k-$\omega$ plot (see FIG. 5) of either the signals or the differenced signals, the array processor 160 determines the wavelength and so the (spatial) wavenumber k, and also the (temporal) frequency and so the angular frequency $\omega$, of various of the spectral components of the stochastic parameter. There are numerous algorithms available in the public domain to perform the spatial/temporal decomposition of arrays of sensor units 118-121.

Figure 5:
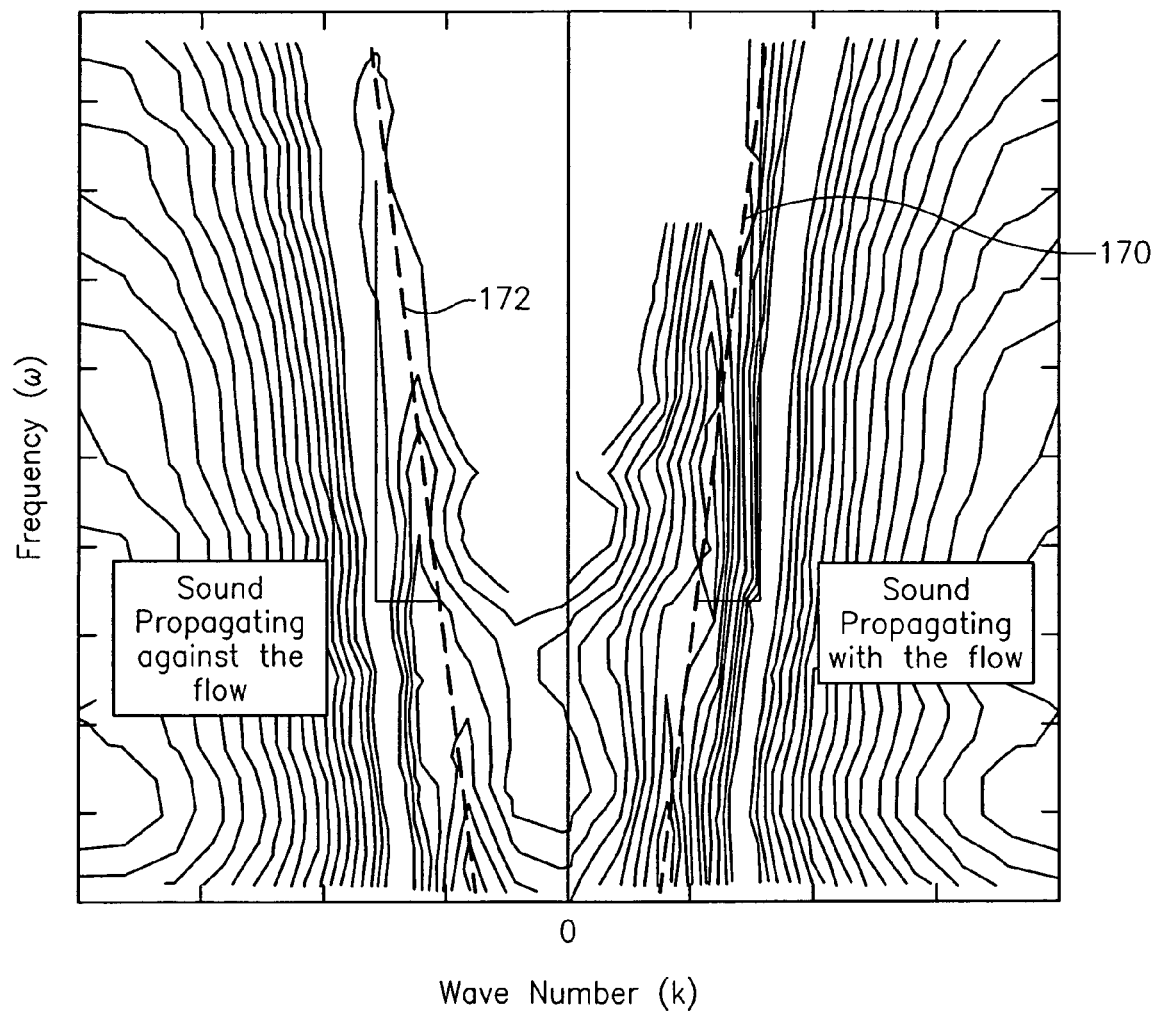
FIG. 5 is a kω plot of data processed from an array of pressure sensors use to measure the speed of sound of a fluid flow passing in a pipe.

In the case of suitable acoustic waves being present in both axial directions, the power in the k-ω plane shown in a k-ω plot of FIG. 5 so determined will exhibit a structure that is called an acoustic ridge 170,172 in both the left and right planes of the plot, wherein one of the acoustic ridges 170 is indicative of the speed of sound traveling in one axial direction and the other acoustic ridge 172 being indicative of the speed of sound traveling in the other axial direction. The acoustic ridges represent the concentration of a stochastic parameter that propagates through the flow and is a mathematical manifestation of the relationship between the spatial variations and temporal variations described above. Such a plot will indicate a tendency for k-ω pairs to appear more or less along a line 170,172 with some slope, the slope indicating the speed of sound.

The power in the k-ω plane so determined is then provided to an acoustic ridge identifier 162, which uses one or another feature extraction method to determine the location and orientation (slope) of any acoustic ridge present in the left and right k-ω plane. The velocity may be determined by using the slope of one of the two acoustic ridges 170,172 or averaging the slopes of the acoustic ridges 170,172.

Finally, information including the acoustic ridge orientation (slope) is used by an analyzer 164 to determine the flow parameters relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

An array processor 160 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

One such technique of determining the speed of sound propagating through the flow 12 is using array processing techniques to define an acoustic ridge in the k-ω plane as shown in FIG. 5. The slope of the acoustic ridge is indicative of the speed of sound propagating through the flow 12. The speed of sound (SOS) is determined by applying sonar arraying processing techniques to determine the speed at which the one dimensional acoustic waves propagate past the axial array of unsteady pressure measurements distributed along the pipe 14.

The apparatus 200 of the present invention measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and flow 12 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While the sonar-based flow meter using an array of sensors 118-121 to measure the speed of sound of an acoustic wave propagating through the mixture is shown and described, one will appreciate that any means for measuring the speed of sound of the acoustic wave may used to determine the entrained gas volume fraction of the mixture/fluid or other characteristics of the flow described hereinbefore.

The analyzer 164 of the processing unit 124 provides output signals indicative of characteristics of the process flow 12 that are related to the measured speed of sound (SOS) propagating through the flow 12. For example, to determine the gas volume fraction (or phase fraction), the analyzer 164 assumes a nearly isothermal condition for the flow 12. As such the gas volume fraction or the void fraction is related to the speed of sound by the following quadratic equation:

$$Ax^2+Bx+C=0$$

wherein x is the speed of sound, $A=1+rg/rl*(K_{eff}/P-1)-K_{eff}/P$, $B=K_{eff}/P-2+rg/rl$; $C=1-K_{eff}/rl*a_{meas}{}^2)$; Rg=gas density, rl=liquid density, $K_{eff}$=effective K (modulus of the liquid and pipewall), P=pressure, and $a_{meas}$=measured speed of sound.

Effectively, $$\text{Gas Volume Fraction (GVF)}=(-B+\text{sqrt}(B^2-4*A*C))/(2*A)$$

Alternatively, the sound speed of a mixture can be related to volumetric phase fraction ($\phi_i$) of the components and the sound speed (a) and densities (ρ) of the component through the Wood equation.

$$\frac{1}{\rho_{mix} a_{mix\infty}^2} = \sum_{i=1}^{N} \frac{\phi_i}{\rho_i a_i^2} \text{ where } \rho_{mix} = \sum_{i=1}^{N} \rho_i \phi_i \qquad (5)$$

For example, the measured density ($\rho_{mix}$) from the first device (e.g., Coriolis meter or gamma densitometer) may be used as an input to this equation.

One dimensional compression waves propagating within a flow 12 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{\frac{1}{a_{mix\infty}^2} + \rho_{mix} \frac{2R}{Et}}} \qquad (6)$$

Figure 6:
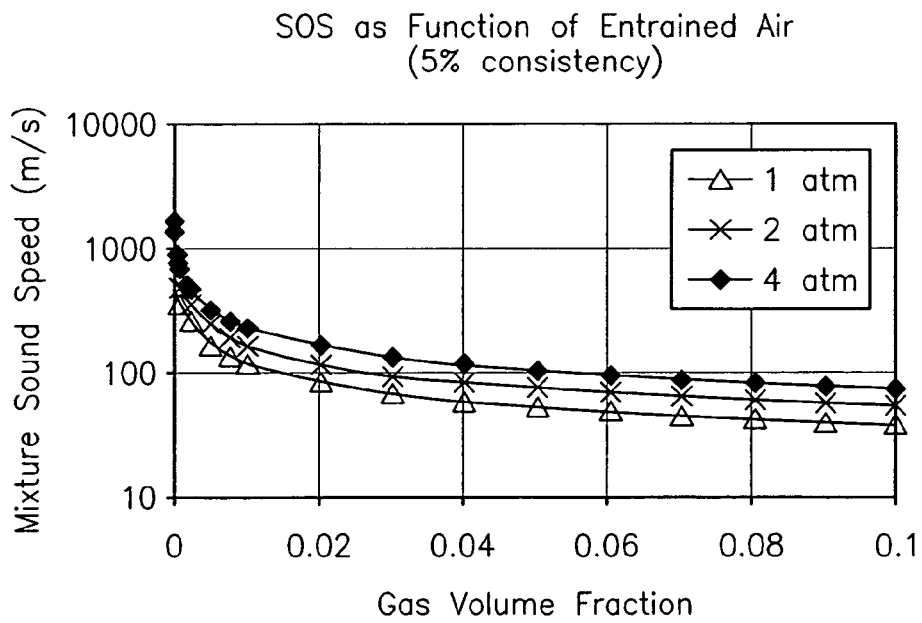
FIG. 6 is a plot of the speed of sound of the fluid flow as a function of the gas volume fraction over a range of different pressures.

The mixing rule essentially states that the compressibility of a mixture ($1/(\rho a^2)$) is the volumetrically-weighted average of the compressibilities of the components. For gas/ liquid mixtures 12 at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained air volume fraction is shown in FIG. 6.

Some or all of the functions within the processing unit 24 may be implemented in software (using a microprocessor or computer) and/or firmware, or may be implemented using analog and/or digital hardware, having sufficient memory, interfaces, and capacity to perform the functions described herein.

In one embodiment of the present invention as shown in FIG. 4, each of the pressure sensors 118-121 may include a piezoelectric film sensor to measure the unsteady pressures of the fluid flow 12 using either technique described hereinbefore. The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 14 due to unsteady pressure variations (e.g., acoustic waves) within the process mixture 12. Strain within the pipe is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. No. 10/712,818 (CiDRA Docket No. CC-0675), U.S. patent application Ser. No. 10/712,833 (CiDRA Docket No. CC-0676), and U.S. patent application Ser. No. 10/795,111 (CiDRA Docket No. CC-0732), which are incorporated herein by reference.

Another embodiment of the present invention include a pressure sensor such as pipe strain sensors, accelerometers, velocity sensors or displacement sensors, discussed hereinafter, that are mounted onto a strap to enable the pressure sensor to be clamped onto the pipe. The sensors may be removable or permanently attached via known mechanical techniques such as mechanical fastener, spring loaded, clamped, clam shell arrangement, strapping or other equivalents. These certain types of pressure sensors, it may be desirable for the pipe 12 to exhibit a certain amount of pipe compliance.

Instead of single point pressure sensors 118-121, at the axial locations along the pipe 12, two or more pressure sensors may be used around the circumference of the pipe 12 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 118-121 of FIG. 4 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 118-121 may be Bragg grating based pressure sensors, such as that described in U.S. patent application, Ser. No. 08/925,598, entitled "High Sensitivity Fiber Optic Pressure Sensor For Use In Harsh Environments", filed Sept. 8, 1997, now U.S. Pat. No. 6,016,702, and in U.S. patent application, Ser. No. 10/224,821, entitled "Non-Intrusive Fiber Optic Pressure Sensor for Measuring Unsteady Pressures within a Pipe", which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 115-118 and it may measure the unsteady (or dynamic or ac) pressure variations inside the pipe or tube 14 by measuring the pressure levels inside of the tube. These sensors may be ported within the pipe to make direct contact with the mixture 12. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the tube, such as highly sensitive piezoelectric, electronic or electric, strain gages attached to or embedded in the tube 14.

While a number of sensor have been described, one will appreciate that any sensor the measures the speed of sound propagating through the fluid may be used with the present invention, including ultrasonic sensors.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring parameters of a mixture flowing in a pipe, the mixture having a plurality of components that includes at least two solids, a liquid, and a gas; the apparatus comprising:
   a first device configured to sense at least one parameter of the mixture indicative of a density of the mixture and provide a first signal indicative of the density;
   a second device configured to sense at least one parameter of the mixture indicative of a combined concentration of the at least two solids in the mixture and provide a second signal indicative of the combined concentration of the solids;
   a third device configured to sense at least one parameter of the mixture indicative of a concentration of the gas in the mixture and provide a third signal indicative of the concentration of the gas; and
   a signal processor that determines a concentration of each of the at least two solids and a concentration of the liquid in response to the first second and third signals, wherein the concentrations of each of the solids and liquid are a function of the density of each component of the mixture and sensitivity parameters.

2. The apparatus of claim 1, wherein the first device includes at least one of a Coriolis meter and a gamma densitometer.

3. The apparatus of claim 1, wherein the at least one parameter sensed by the second device includes at least one of: capacitance of the mixture, conductance of the mixture, absorption of energy applied to the mixture, attenuation of energy applied to the mixture, time delay of energy applied to the mixture, and phase delay of energy applied to the mixture.

4. The apparatus of claim 1, wherein the second device includes a consistency meter.

5. The apparatus of claim 1, wherein the signal processor is further configured to determine a volumetric flow rate of each of the at least two solids using the concentration of each of the at least two solids or a volumetric flow rate of the liquid using the concentration of the liquid.

6. The apparatus of claim 1, wherein the signal processor uses the following equations for determining said concentrations of the solids and liquids:

$$\begin{bmatrix} \rho_L & \rho_{S1} & \rho_{S2} & \rho_{gas} \\ \alpha_L \frac{\rho_L}{\rho_{mix}} & \alpha_{S1} \frac{\rho_{S1}}{\rho_{mix}} & \alpha_{S2} \frac{\rho_{S2}}{\rho_{mix}} & \alpha_{gas} \frac{\rho_{gas}}{\rho_{mix}} \\ 0 & 0 & 0 & 1 \\ 1 & 1 & 1 & 1 \end{bmatrix} \begin{Bmatrix} \phi_L \\ \phi_{S1} \\ \phi_{S2} \\ \phi_{gas} \end{Bmatrix} = \begin{Bmatrix} \rho_{mix} \\ Cs \\ GVF \\ 1 \end{Bmatrix}$$

Wherein $\rho_L$, $\rho_{S1}$, $\rho_{S2}$, $\rho_{gas}$ is the density of the liquid, first solid, second solid, and gas, respectively, $\alpha_L$, $\alpha_{S1}$, $\alpha_{S2}$, $\alpha_{gas}$ is the sensitivity parameter of the liquid, first solid, second solid and gas, respectively; $\phi_L$, $\phi_{S1}$, $\phi_{S2}$, $\phi_{gas}$ the concentration of the liquid, first solid, second solid, and gas, respectively; $\rho_{mix}$, is the density of mixture; Cs is the concentration of the solids; and GVF is the phase fraction of the gas.

7. The apparatus of claim 1, wherein the at least one parameter sensed by the third device includes a speed of sound propagating through the mixture.

8. The apparatus of claim 7, wherein the third device includes a spatial array of at least two pressure sensors disposed at different axial locations along the pipe, each of the at least two pressure sensors providing a pressure signal indicative of unsteady pressure within the pipe at a corresponding axial location, the unsteady pressure being caused at least in part by acoustic pressure disturbances in the mixture.

9. The apparatus of claim 8, wherein the spatial array of pressure sensors include three pressure sensors disposed at different axial locations along the pipe.

10. The apparatus of claim 8, wherein the spatial array of pressure sensors include 4, 5, 6, 7, 8, 9, 10, 11, 12, 13, 14, 15, or 16 pressure sensors disposed at different axial locations along the pipe.

11. The apparatus of claim 8, wherein the acoustic pressure disturbances include a one-dimensional acoustic wave propagating through the mixture.

12. The apparatus of claim 8, wherein the entrained gas meter, in response to the pressure signals, determines the slope of an acoustic ridge in k-ω plane to determine the speed of sound of the acoustic wave propagating through the fluid.

13. A method for measuring parameters of a mixture flowing in a pipe, the mixture having a plurality of components that including at least two solids, a liquid, and a gas, the method comprising:

sensing at least one parameter of the mixture indicative of a density of the mixture and providing a first signal indicative of the density;

sensing at least one parameter of the mixture indicative of a combined concentration of the at least two solids in the mixture and providing a second signal indicative of the combined concentration of the solids;

sensing at least one parameter of the mixture indicative of a concentration of the gas in the mixture and providing a third signal indicative of the concentration of the gas; and determining a concentration of each of the at least two solids and a concentration of the liquid, in response to the first, second and third signals, wherein the concentrations of each of the solids and liquid are a function of the density of each component of the mixture and sensitivity parameters.

14. The method of claim 13, wherein the at least one parameter of the mixture indicative of the density of the mixture is sensed using at least one of a Coriolis meter and a gamma densitometer.

15. The method of claim 13, wherein the at least one parameter of the mixture indicative of the combined concentration of the at least two solids is sensed using a consistency meter.

16. The method of claim 13, wherein the at least one parameter of the mixture indicative of the concentration of the gas in the mixture includes a speed of sound propagating through the mixture.

17. The method of claim 13, further including using the following equations for determining said concentrations of the solids and liquids:

$$\begin{bmatrix} \rho_L & \rho_{S1} & \rho_{S2} & \rho_{gas} \\ \alpha_L \dfrac{\rho_L}{\rho_{mix}} & \alpha_{S1} \dfrac{\rho_{S1}}{\rho_{mix}} & \alpha_{S2} \dfrac{\rho_{S2}}{\rho_{mix}} & \alpha_{gas} \dfrac{\rho_{gas}}{\rho_{mix}} \\ 0 & 0 & 0 & 1 \\ 1 & 1 & 1 & 1 \end{bmatrix} \begin{Bmatrix} \phi_L \\ \phi_{S1} \\ \phi_{S2} \\ \phi_{gas} \end{Bmatrix} = \begin{Bmatrix} \rho_{mix} \\ Cs \\ GVF \\ 1 \end{Bmatrix}$$

Wherein $\rho_L, \rho_{S1}, \rho_{S2}, \rho_{gas}$ is the density of the liquid, first solid, second solid, and gas, respectively, $\alpha_L, \alpha_{S1}, \alpha_{S2}, \alpha_{gas}$ is the sensitivity parameter of the liquid, first solid, second solid and gas, respectively; $\phi_L, \phi_{S1}, \phi_{S2}, \phi_{gas}$ is the concentration of the liquid, first solid, second solid, and gas, respectively; $\rho_{mix}$ is the density of mixture; Cs is the concentration of the solids; and GVF is the phase fraction of the gas.

18. An apparatus for measuring parameters of a mixture flowing in a pipe, the mixture having a plurality of components that includes at least two solids, a liquid, and a gas, the apparatus comprising:

a density meter that provides a first signal indicative of a density of the mixture;

a consistency meter that provides a second signal indicative of the combined concentration of the solids;

an entrained gas meter that provides a third signal indicative of the concentration of the gas; and a signal processor that determines a concentration of each of the at least two solids and a concentration of the liquid in response to the first second and third signals, wherein the concentrations of each of the solids and liquid are a function of the density of each component of the mixture and sensitivity parameters.

19. The apparatus of claim 18, wherein the density meter includes at least one of a Coriolis meter and a gamma densitometer.

20. The apparatus of claim 18, wherein the signal processor is further configured to determine a volumetric flow rate of each of the at least two solids using the concentration of each of the at least two solids or a volumetric flow rate of the liquid using the concentration of the liquid.

21. The apparatus of claim 18, wherein the signal processor uses the following equations for determining said concentrations of the solids and liquids:

$$\begin{bmatrix} \rho_L & \rho_{S1} & \rho_{S2} & \rho_{gas} \\ \alpha_L \dfrac{\rho_L}{\rho_{mix}} & \alpha_{S1} \dfrac{\rho_{S1}}{\rho_{mix}} & \alpha_{S2} \dfrac{\rho_{S2}}{\rho_{mix}} & \alpha_{gas} \dfrac{\rho_{gas}}{\rho_{mix}} \\ 0 & 0 & 0 & 1 \\ 1 & 1 & 1 & 1 \end{bmatrix} \begin{Bmatrix} \phi_L \\ \phi_{S1} \\ \phi_{S2} \\ \phi_{gas} \end{Bmatrix} = \begin{Bmatrix} \rho_{mix} \\ Cs \\ GVF \\ 1 \end{Bmatrix}$$

Wherein $\rho_L, \rho_{S1}, \rho_{S2}, \rho_{gas}$ is the density of the liquid, first solid, second solid, and gas, respectively, $\alpha_L, \alpha_{S1}, \alpha_{S2}, \alpha_{gas}$ is the sensitivity parameter of the liquid, first solid, second solid and gas, respectively; $\phi_L, \phi_{S1}, \phi_{S2}, \phi_{gas}$ is the concentration of the liquid, first solid, second solid, and gas, respectively; $\rho_{mix}$ is the density of mixture; Cs is the concentration of the solids; and GVF is the phase fraction of the gas.

22. The apparatus of claim 18, wherein the consistency meter senses at least one of: capacitance of the mixture, conductance of the mixture, absorption of energy applied to the mixture, attenuation of energy applied to the mixture, time delay of energy applied to the mixture, and phase delay of energy applied to the mixture.

23. The apparatus of claim 22, wherein the spatial array of pressure sensors include three pressure sensors disposed at different axial locations along the pipe.

24. The apparatus of claim 22, wherein the spatial array of pressure sensors include 4, 5, 6, 7, 8, 9, 10, 11, 12, 13, 14, 15, or 16 pressure sensors disposed at different axial locations along the pipe.

25. The apparatus of claim 22, wherein the acoustic pressure disturbances include a one-dimensional acoustic wave propagating through the mixture.

26. The apparatus of claim 22, wherein the entrained gas meter, in response to the pressure signals, determines the slope of an acoustic ridge in k-ω plane to determine the speed of sound of the acoustic wave propagating through the fluid.

27. The apparatus of claim 18, wherein the entrained gas meter determines a speed of sound propagating through the mixture.

28. The apparatus of claim 27, wherein the entrained gas meter includes a spatial array of at least two pressure sensors disposed at different axial locations along the pipe, each of the at least two pressure sensors providing a pressure signal indicative of unsteady pressure within the pipe at a corresponding axial location, the unsteady pressure being caused at least in part by acoustic pressure disturbances in the mixture.

* * * * *